(12) United States Patent
Hopkins

(10) Patent No.: US 11,756,104 B1
(45) Date of Patent: Sep. 12, 2023

(54) METHOD, APPARATUS, AND COMPUTER PROGRAM PRODUCT FOR CONSTRUCTING AN UPDATED ORDER INCLUDING INFORMATION FROM DIFFERENT SOURCES

(71) Applicant: McKesson Corporation, Irving, TX (US)

(72) Inventor: Stacy Hopkins, Tucker, GA (US)

(73) Assignee: MCKESSON CORPORATION, Irving, TX (US)

( * ) Notice: Subject to any disclaimer, the term of this patent is extended or adjusted under 35 U.S.C. 154(b) by 36 days.

(21) Appl. No.: 16/878,778

(22) Filed: May 20, 2020

(51) Int. Cl.
*G06Q 30/0601* (2023.01)
*G16H 20/10* (2018.01)
*G06F 40/103* (2020.01)

(52) U.S. Cl.
CPC ..... *G06Q 30/0637* (2013.01); *G06Q 30/0603* (2013.01); *G06F 40/103* (2020.01); *G16H 20/10* (2018.01)

(58) Field of Classification Search
CPC .......... G06Q 30/0637; G06Q 30/0603; G06Q 30/0601–0645; G06F 40/103; G16H 20/10
USPC ................................................. 705/26.1–27.2
See application file for complete search history.

(56) References Cited

U.S. PATENT DOCUMENTS

| | | | | |
|---|---|---|---|---|
| 6,973,435 B1 * | 12/2005 | Sioufi | ..................... | G06Q 30/06 705/2 |
| 7,769,601 B1 * | 8/2010 | Bleser | ..................... | G16H 70/40 705/3 |
| 8,219,422 B2 * | 7/2012 | Hallberg | ................ | G06Q 40/08 705/4 |
| 8,660,859 B1 * | 2/2014 | Ansari | ................... | G16H 10/60 705/2 |

(Continued)

FOREIGN PATENT DOCUMENTS

| | | |
|---|---|---|
| CA | 2495018 C | 6/2013 |
| CA | 2552056 C | 6/2015 |

(Continued)

OTHER PUBLICATIONS

PPD "PPD Collaborates with CISYS LifeSciences to Implement New Web-based Event Adjudication System" BusinessWire.com (Year: 2015).*

(Continued)

*Primary Examiner* — Allison G Wood
*Assistant Examiner* — Katherine A Barlow
(74) *Attorney, Agent, or Firm* — ALSTON & BIRD LLP

(57) ABSTRACT

A method, apparatus and computer program product provide for monitoring an adjudication network. In relation to a method, first information is caused to be provided by a request processor in response to an inquiry to be provided to a source. The method also receives an order including second information, different than the first information, from the source. The method further combines at least some of the second information with at least some of the first informa- (Continued)

tion to form an updated order and transmits the updated order to a supplier. Additionally, the method monitors the adjudication network, such as for a predefined period of time, to determine a status of the updated order and provides a notification to the source in response to the updated order having a predefined status.

17 Claims, 6 Drawing Sheets

(56) References Cited

U.S. PATENT DOCUMENTS

| | | | | |
|---|---|---|---|---|
| 8,781,851 | B2* | 7/2014 | Anderson | G16H 20/10 705/2 |
| 10,438,693 | B1* | 10/2019 | Vandervoort | G16H 10/60 |
| 2004/0006490 | A1* | 1/2004 | Gingrich | G16H 40/67 705/2 |
| 2004/0172301 | A1* | 9/2004 | Mihai | G16H 20/10 705/2 |
| 2012/0016687 | A1 | 1/2012 | Dhavle et al. | |
| 2013/0179177 | A1 | 7/2013 | Dhavle et al. | |
| 2016/0055314 | A1 | 2/2016 | Anderson et al. | |
| 2016/0117472 | A1* | 4/2016 | Padmani | G16H 20/10 705/2 |
| 2016/0188820 | A1 | 6/2016 | Brown et al. | |
| 2017/0098043 | A1 | 4/2017 | Antony et al. | |
| 2017/0329921 | A1 | 11/2017 | Willard et al. | |
| 2018/0075215 | A1 | 3/2018 | Loiacono et al. | |
| 2018/0293351 | A1 | 10/2018 | Simons et al. | |
| 2018/0293358 | A1* | 10/2018 | Sooudi | G06Q 30/0267 |
| 2019/0333158 | A1* | 10/2019 | Cedergreen | G16H 20/10 |
| 2023/0059605 | A1 | 2/2023 | Sait et al. | |

FOREIGN PATENT DOCUMENTS

| | | |
|---|---|---|
| CA | 2900718 A1 | 2/2016 |
| CA | 2552057 C | 8/2016 |
| WO | WO 2012/009513 A1 | 1/2012 |

OTHER PUBLICATIONS

Transaction Data Systems. "Computer-Rx Empowers Community Pharmacies with Digital Communications Solutions from Updox" PRNewsWire.com (Year: 2018).*

Bahga, A. et al. "A Cloud-based Approach for Interoperable Electronic Health Records (EHRs)," in IEEE Journal of Biomedical and Health Informatics, vol. 17, No. 5, pp. 894-906, doi: 10.1109/JBHI.2013.2257818. (Year: 2013).*

Klann, Jeffrey G., et al. "Supporting Multi-sourced Medication Information in i2b2." AMIA Annu Symp Proc. 2015:747-55. PMID: 26958210; PMCID: PMC4765563. (Year: 2015).*

U.S. Appl. No. 16/832,318, "Method, Apparatus, and Computer Program Product for Providing Estimated Prescription Costs", Unpublished (filed Mar. 27, 2020), (Stacy Hopkins, Inventor) (McKesson Corporation, Assignee).

U.S. Appl. No. 17/201,020, "Method, Apparatus, and Computer Program Product for Constructing an Updated Order Verifying Compliance With Predefined Rule(s)", Unpublished (filing date Mar. 15, 2021), (Stacy Hopkins, Inventor), (McKesson Corporation, Assignee).

U.S. Appl. No. 17/205,457, "Computing Device, Method and Computer Program Product for Constructing a Consolidated Message", Unpublished (filing date Mar. 18, 2021), (Stacy Hopkins, Inventor), (McKesson Corporation, Assignee).

United States Patent and Trademark Office, Non-Final Office Action received for U.S. Appl. No. 17/205,457, dated Apr. 12, 2023, 33 pages, US.

* cited by examiner

METHOD, APPARATUS, AND COMPUTER PROGRAM PRODUCT FOR CONSTRUCTING AN UPDATED ORDER INCLUDING INFORMATION FROM DIFFERENT SOURCES

TECHNOLOGICAL FIELD

An example embodiment relates generally to the construction of an updated order including information from different sources and, more particularly, to the construction and submission of the updated order and the subsequent monitoring of an adjudication network to determine the order status.

BACKGROUND

Two or more parties frequently communicate with one another via messages exchanged over a communication network for a wide variety of different purposes. For example, one party may formulate a request to be transmitted to another party and may then await a response to the request from the other party. In order to allow the request to be processed such that a response that is both accurate and complete is provided, each party must be configured to communicate in accordance with the same set of rules, e.g., in accordance with the same communications standard, such as utilizing the same format and syntax, utilizing the same message construct including the same fields conveying predefined types of information, etc.

However, the standards that govern communication between parties continue to evolve and the standards are repeatedly updated to allow for more efficient, reliable and secure communications. However, not all parties may be advised of and implement the updated communication standards or at least may not be advised of and implement the updated communication standards at the same time as other parties with some parties more quickly adopting the updated standards than other parties. In this instance, the parties attempting to communicate may fail to do so or may do so in an inefficient manner as a result of the different parties endeavoring to communicate in accordance with different standards.

Additional inefficiencies in inter-party communications may be introduced in an instance in which one party makes a request of another party and then awaits a response. In these instances, the requesting party may misinterpret a period of silence and a lack of a quick response from the other party as an indication that either the request or the response was misdirected with the requesting party believing that it will fail to receive a response in either instance. In this situation, the requesting party may repeat the request one or more additional times. These additional requests may oftentimes be unnecessary as the delay in the provision of the response may simply be due to processing performed by the other party to formulate the response and may not be indicative of any failure of communications. Thus, the additional requests may disadvantageously consume additional bandwidth and other resources of the communication network and, in some instances, may also unnecessarily consume additional computing resources of the party that receives the additional requests in relation to repeatedly processing the same request and potentially providing multiple responses thereto. As a result, the efficiency with which the parties communicate may be correspondingly reduced.

BRIEF SUMMARY

A method, apparatus and computer program product are provided in accordance with an example embodiment in order to provide for more efficient communication between parties. In this regard, each party may communicate in the standard with which the respective party is configured with the method, apparatus and computer program product of an example embodiment providing for any necessary conversion between the parties, including the construction of a message including information provided by two or more sources, to facilitate efficient communication between the parties even in an instance in which the parties operate in accordance with different communication standards. The method, apparatus and computer program and product of an example embodiment are also configured to provide for efficient utilization of the communication network and the computing resources of the parties by monitoring an adjudication network in response to the submission of an order by a requesting party to determine an order status and providing a notification to the requesting party of the order status, thereby limiting the instances in which the requesting party will transmit a repeated request that may otherwise unnecessarily consume communication network and/or computing resources.

In an example embodiment, a method is provided for monitoring an adjudication network. The method includes causing first information provided by a request processor in response to an inquiry to be provided to a source. The method also receives an order including second information, different than the first information, from the source. The method further combines at least some of the second information with at least some of the first information to form an updated order and transmits the updated order to a supplier. Additionally, the method monitors the adjudication network, such as for a predefined period of time, to determine a status of the updated order and provides a notification to the source in response to the updated order having a predefined status.

In an embodiment in which the order is received in accordance with a first format, the method further includes converting the order to a second format, different than the first format prior to formation of the updated order. The method of an example embodiment also includes storing the first information provided by the request processor such that the method of this example embodiment combines at least some of the second information with at least some of the first information by accessing the first information that has been stored. In an example embodiment, the method also includes processing the order to identify whether all required data elements have been provided and, in an instance in which one or more of the required data elements have not been provided, communicating with the source to obtain the one or more required data elements prior to combining the at least some of the second information with at least some of the first information. The method of an example embodiment also includes determining whether the source and the supplier are able to utilize the updated order and, in an instance in which the source and the supplier are able to utilize the updated order, providing an indication to the source in association with the first information. In an example embodiment, the method additionally includes identifying the supplier based upon the second information of the order and accessing predetermined routing information to identify address information associated with the supplier.

In another example embodiment, an apparatus is provided that is configured to monitor an adjudication network. The apparatus includes a communication interface configured to cause first information provided by a request processor in response to an inquiry to be provided to a source and to receive an order including second information, different than the first information, from the source. The apparatus also includes processing circuitry configured to combine at least some of the second information with at least some of the first information to form an updated order for transmission by the communication interface to a supplier. The processing circuitry is also configured to monitor the adjudication network, such as for a predefined period of time, to determine a status of the updated order. The communication interface is also configured to provide a notification to the source in response to the updated order being determined by the processing circuitry to have a predefined status.

In an example embodiment in which the order is received in accordance with a first format, the processing circuitry is further configured to convert the order to a second format, different than the first format prior to formation of the updated order. The apparatus of an example embodiment may also include a memory device configured to store the first information provided by the request processor with the processing circuitry being configured to combine at least some of the second information with at least some of the first information by accessing the first information that has been stored by the memory device. The processing circuitry of an example embodiment is further configured to process the order to identify whether all required data elements have been provided and, in an instance in which one or more of the required data elements have not been provided, the communication interface is further configured to communicate with the source to obtain the one or more required data elements prior to combining the at least some of the second information with at least some of the first information. In an example embodiment, the processing circuitry is further configured to determine whether the source and the supplier are able to utilize the updated order and the communication interface is further configured, in an instance in which the source and the supplier are able to utilize the updated order, to provide an indication to the source in association with the first information. The processing circuitry of an example embodiment is further configured to identify the supplier based upon the second information of the order and to access predetermined routing information to identify address information associated with the supplier.

In a further example embodiment, a computer program product is provided that is configured to monitor an adjudication network. The computer program product includes at least one non-transitory computer-readable storage medium having computer-executable program code instructions stored therein with the computer-executable program code instructions including program code instructions configured to cause first information provided by a request processor in response to an inquiry to be provided to a source. The program code instructions are also configured to receive an order including second information, different than the first information, from the source. The program code instructions are further configured to combine at least some of the second information with at least some of the first information to form an updated order and to cause the updated order to be transmitted a supplier. Additionally, the program code instructions are configured to monitor the adjudication network, such as for a predefined period of time, to determine a status of the updated order and to cause a notification to be provided to the source in response to the updated order having a predefined status.

In an embodiment in which the order is received in accordance with a first format, the program code instructions are further configured to convert the order to a second format, different than the first format prior to formation of the updated order. In an example embodiment, the program code instructions are further configured to store the first information provided by the request processor, and the program code instructions configured to combine at least some of the second information with at least some of the first information include program code instructions configured to access the first information that has been stored. The program code instructions of an example embodiment that are configured to monitor the adjudication network include program code instructions configured to monitor the adjudication network for a predefined period of time.

The program code instructions of an example embodiment are further configured to process the order to identify whether all required data elements have been provided and, in an instance in which one or more of the required data elements have not been provided, cause the source to be alerted to solicit the one or more required data elements prior to combining the at least some of the second information with at least some of the first information. In an example embodiment, the program code portions are further configured to determine whether the source and the supplier are able to utilize the updated order and, in an instance in which the source and the supplier are able to utilize the updated order, cause an indication to be provided to the source in association with the first information.

BRIEF DESCRIPTION OF THE DRAWINGS

Figure 1:
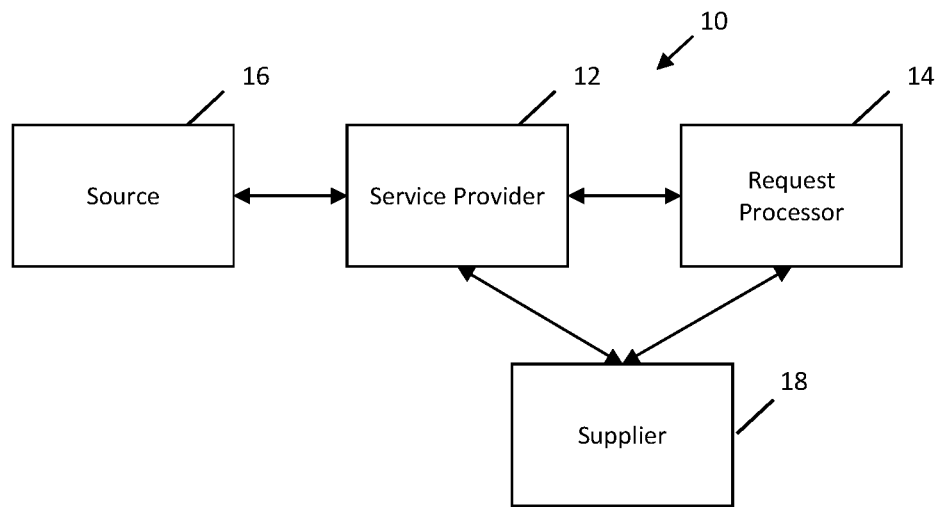
Figure 2:
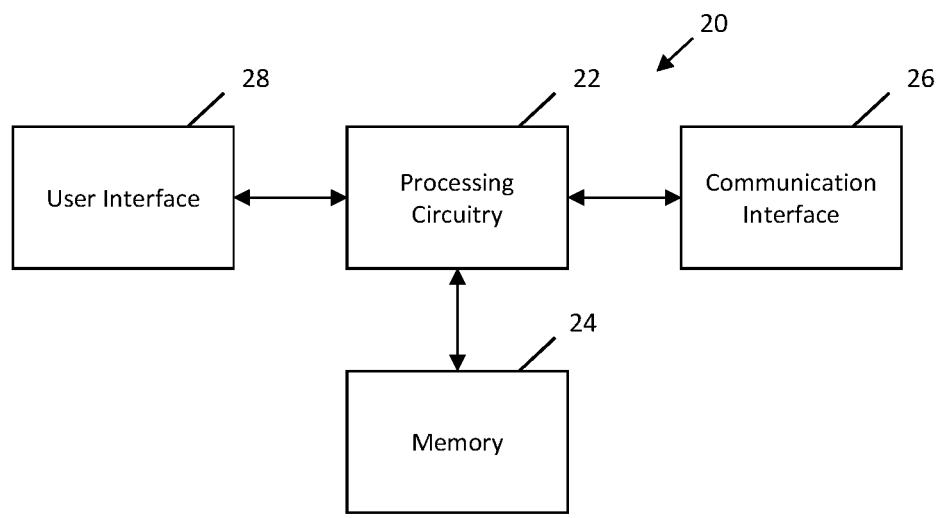
Figure 3:
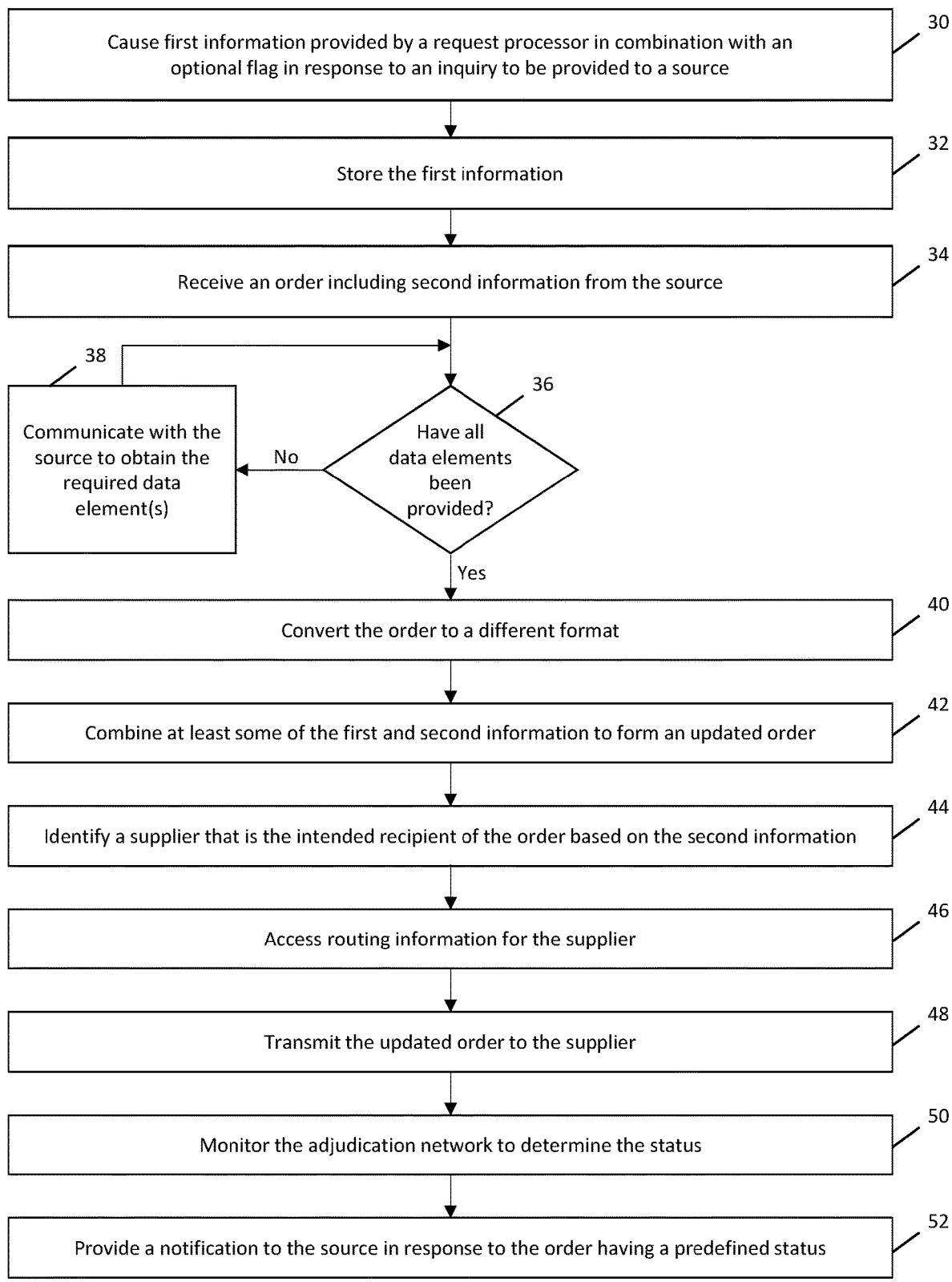
Figure 4:
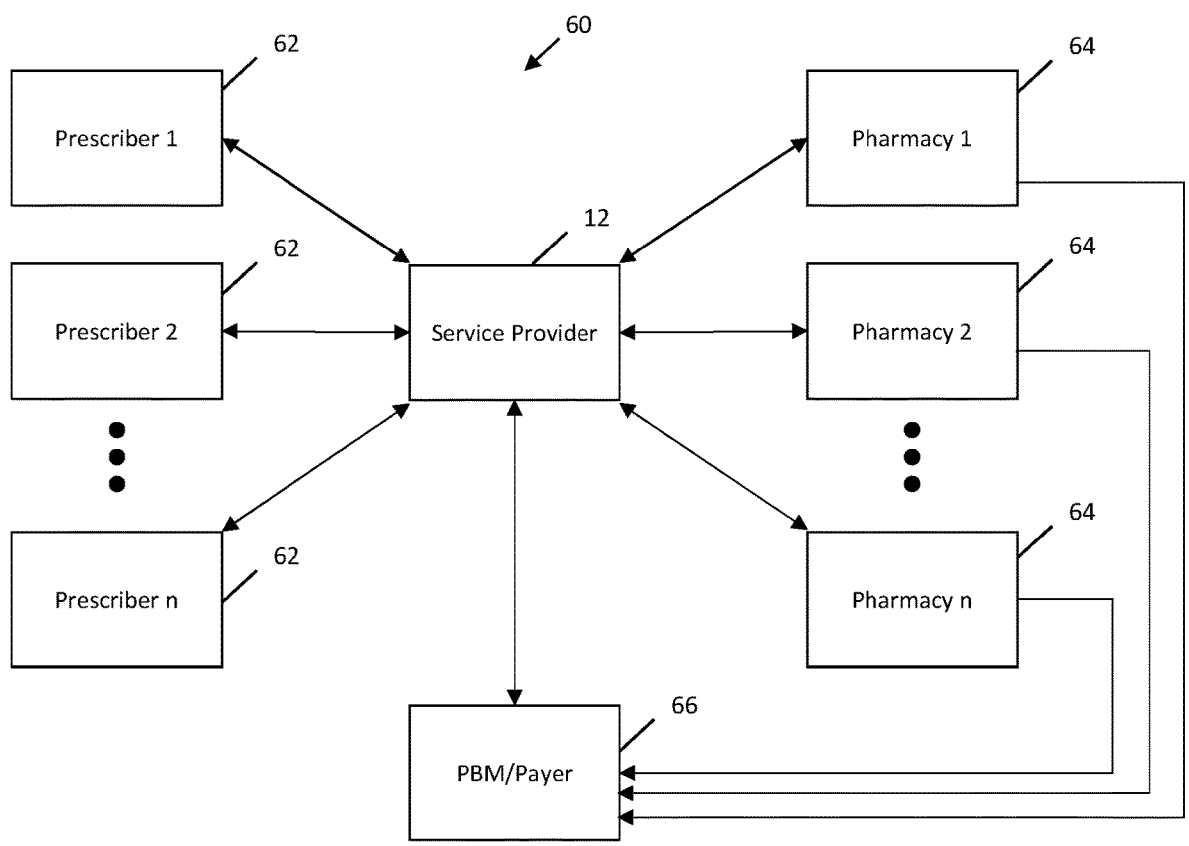
Figure 5A:
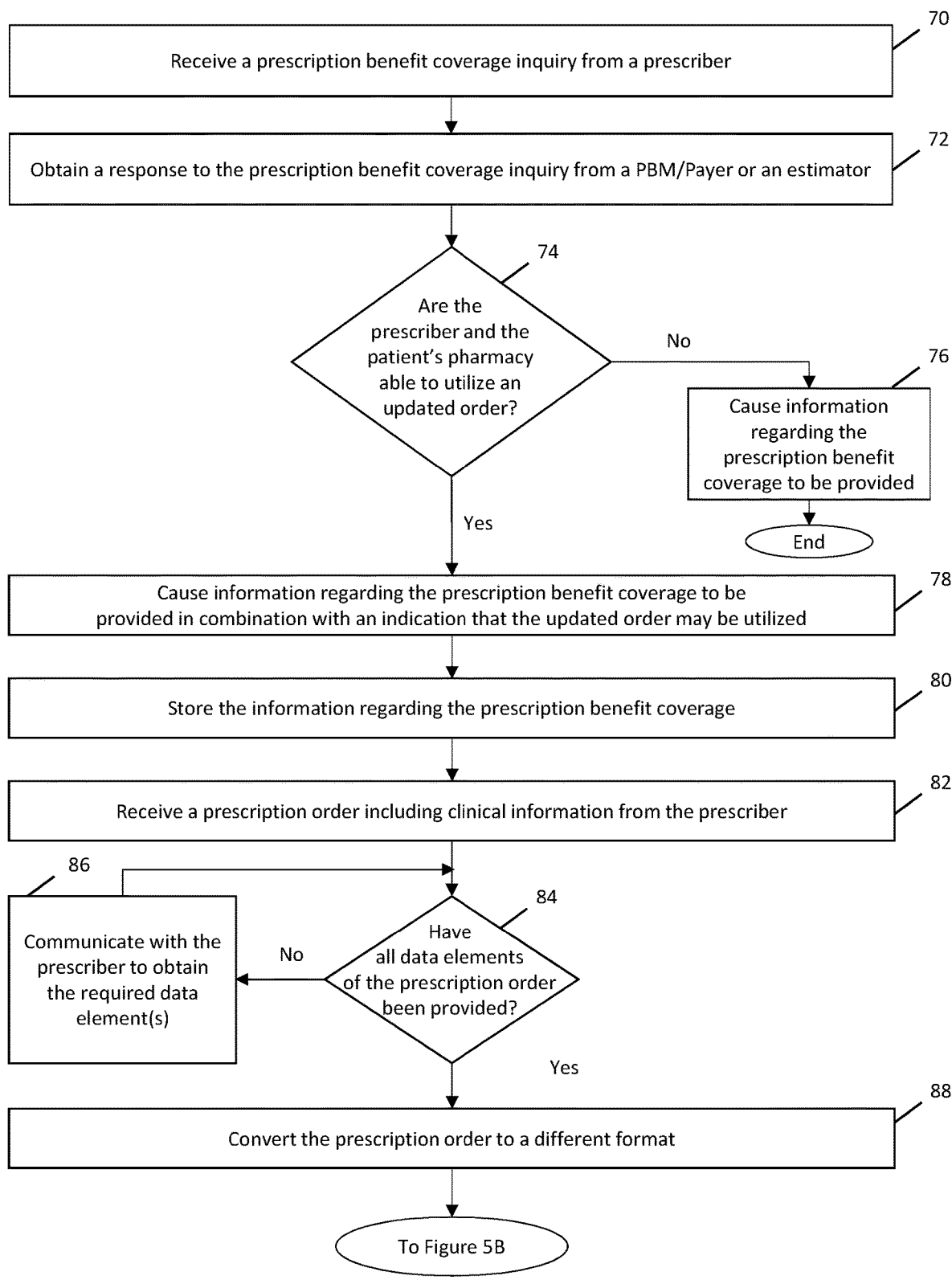
Figure 5B:
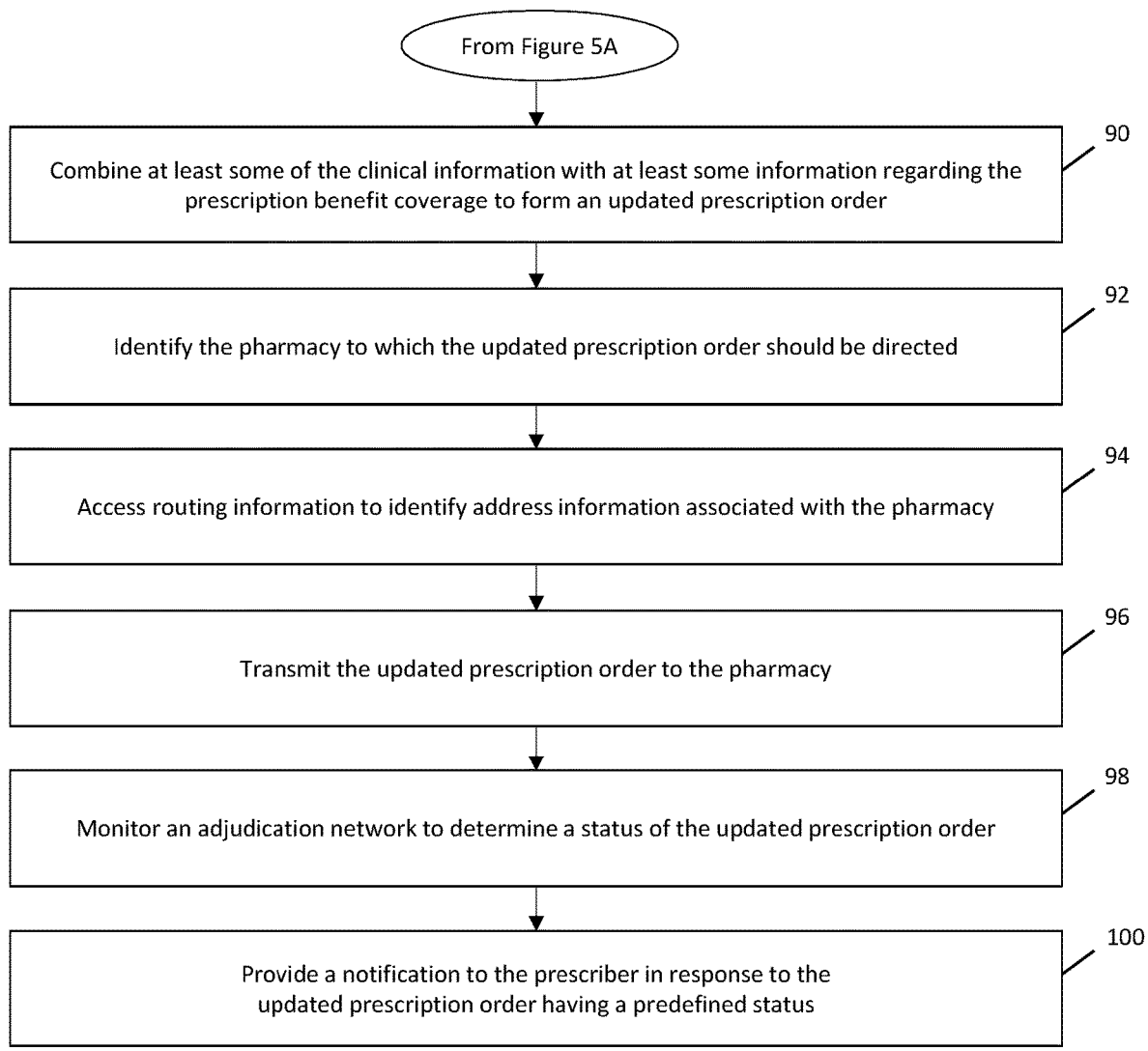
Figure 6:
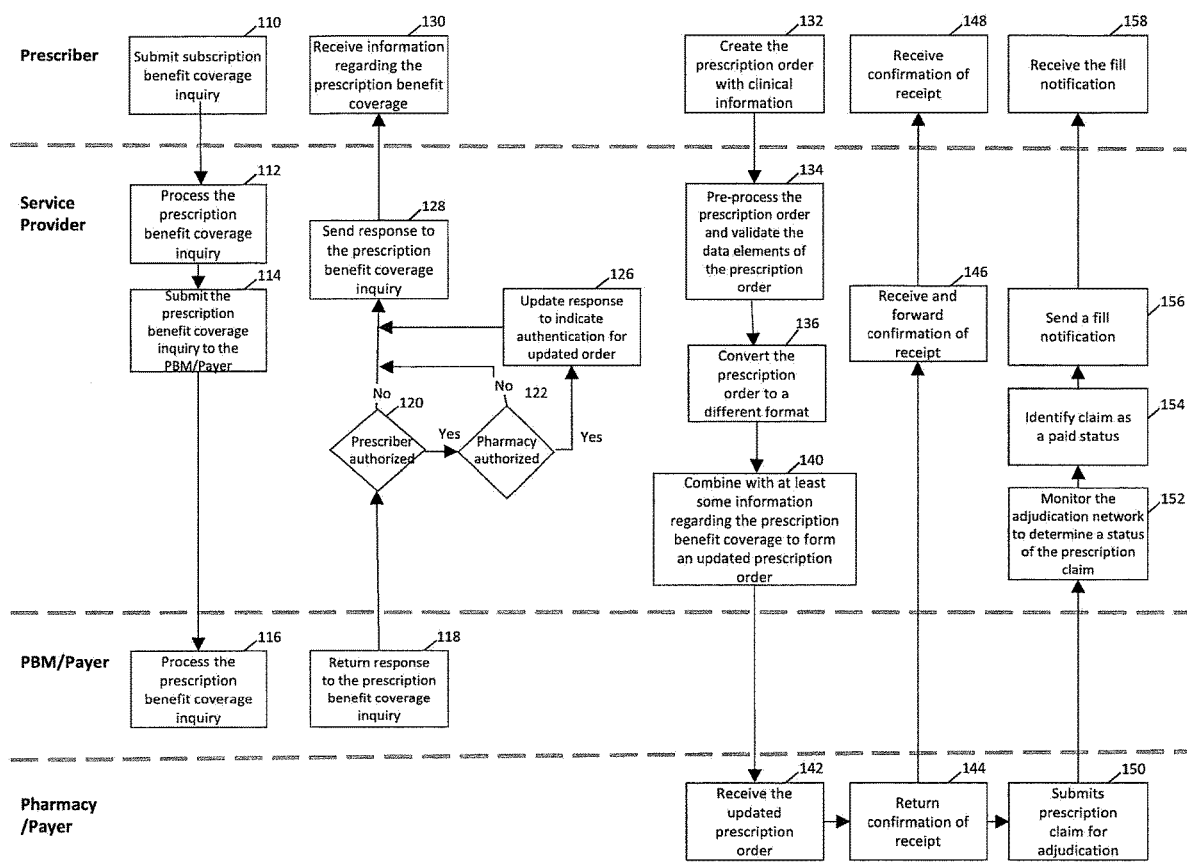

Having thus described certain embodiments of the invention in general terms, reference will now be made to the accompanying drawings, which are not necessarily drawn to scale, and wherein:

FIG. 1 is a block diagram of a system including an apparatus that may be specifically configured in accordance with an example embodiment in order to facilitate communication between multiple parties;

FIG. 2 is a block diagram of an apparatus that may be specifically configured in accordance with an example embodiment in order to facilitate communication between multiple parties;

FIG. 3 is a flowchart of the operations performed, such as by the apparatus of FIG. 2, in accordance with an example embodiment;

FIG. 4 is a block diagram of a system including an apparatus in accordance with an example embodiment in order to facilitate communications between one or more prescribers, one or more pharmacies, and one or more pharmacy benefit management entities or payers in order to efficiently adjudicate a prescription order;

FIGS. 5A and 5B are flowcharts illustrating the operations performed, such as by the apparatus of FIG. 2, in accordance with an example embodiment; and FIG. 6 is a flow diagram illustrating the interaction between a prescriber, a prescription benefits management entity or payer, a prescriber and an apparatus specifically configured in accordance with an example embodiment.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

A method, apparatus in computer program product are provided in accordance with an example embodiment in order to construct a message, such as an updated order, that includes information from at least two different sources and, following transmission of the message, to monitor an adjudication network in order to determine the order status. In relation to constructing the message, the method, apparatus and computer program product of an example embodiment are configured to include information provided by at least two different sources and to convert at least a portion of the message to a different format. Thus, the method, apparatus and computer program product of this example embodiment provide for efficient communication between different parties, even in an instance in which the different parties communicate in accordance with differently formatted messages, such as messages constructed in accordance with different standards. By monitoring the adjudication network and providing a notification of the order status, the method, apparatus and computer program product of an example embodiment provide assurance to the party that transmitted the original message that the message is being processed and a response will be provided, thereby reducing the incentive to repeatedly transmit the same message and correspondingly conserving communication network resources, such as bandwidth, as well as resources otherwise expended by that computing devices that would process the repeatedly transmitted messages.

The method, apparatus and computer program product of an example embodiment may be utilized in conjunction with the construction of messages and the monitoring of the subsequent adjudication in a wide variety of different applications. For example, the method, apparatus and computer program product of an example embodiment may be employed in conjunction with the construction and subsequent monitoring of messages in conjunction with telecommunication applications, content delivery and provisioning and healthcare applications, such as in conjunction with the submission and evaluation of prescription claims, such as a prescription claim submitted by a prescriber, and the provision of feedback regarding reimbursement of the patient by a request processor in the form of a pharmacy benefit manager, a claims payer, e.g., an insurance company or the like, to name but a few.

One example of a system 10 in which the method, apparatus and computer program product of an example embodiment may be deployed is depicted in FIG. 1. As shown, the system includes a service provider 12 that includes or is embodied by the apparatus and is configured to communicate with a plurality of different parties, such as a request processor 14, a source 16 and a supplier 18. The apparatus of the service provider of an example embodiment may, in turn, be embodied by any of variety of different computing devices including, for example, a server, a plurality of networked computing devices, a computer workstation or the like. Regardless of the computing device that embodies the apparatus, the apparatus 20 of the service provider of an example embodiment includes, is associated with or is otherwise in communication with processing circuitry 22, memory 24, communication interface 26 and optionally a user interface 28 as shown, for example, by FIG. 2.

In some embodiments, the processing circuitry 22 (and/or co-processors or any other processors assisting or otherwise associated with the processing circuitry) can be in communication with the memory 24 via a bus for passing information among components of the apparatus 20. The memory can be non-transitory and can include, for example, one or more volatile and/or non-volatile memories. In other words, for example, the memory may be an electronic storage device (for example, a computer readable storage medium) comprising gates configured to store data (for example, bits) that can be retrievable by a machine (for example, a computing device like the processing circuitry). The memory can be configured to store information, data, content, applications, instructions, or the like for enabling the apparatus to carry out various functions in accordance with an example embodiment of the present disclosure. For example, the memory can be configured to buffer input data for processing by the processing circuitry. Additionally or alternatively, the memory can be configured to store instructions for execution by the processing circuitry.

The processing circuitry 22 can be embodied in a number of different ways. For example, the processing circuitry may be embodied as one or more of various hardware processing means such as a processor, a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like. As such, in some embodiments, the processing circuitry can include one or more processing cores configured to perform independently. Alternatively, the processing circuitry can include one or more processors configured in tandem via the bus to enable independent execution of instructions.

In an example embodiment, the processing circuitry 22 can be configured to execute instructions stored in the memory 24 or otherwise accessible to the processing circuitry. Alternatively or additionally, the processing circuitry can be configured to execute hard coded functionality. As such, whether configured by hardware or software methods, or by a combination thereof, the processing circuitry can represent an entity (for example, physically embodied in circuitry) capable of performing operations according to an embodiment of the present disclosure while configured accordingly. Thus, for example, when the processing circuitry is embodied as an ASIC, FPGA or the like, the processing circuitry can be specifically configured hardware for conducting the operations described herein. Alternatively, as another example, when the processing circuitry is embodied as an executor of software instructions, the instructions can specifically configure the processing circuitry to perform the algorithms and/or operations described herein when the instructions are executed. However, in some cases, the processing circuitry can be a processor of a specific device (for example, the service provider 12) configured to employ an embodiment of the present disclosure by further configuration of the processor by instructions for performing the algorithms and/or operations described herein. The processing circuitry can include, among other things, a clock, an arithmetic logic unit (ALU) and/or one or more logic gates configured to support operation of the processing circuitry.

The apparatus 20 of an example embodiment can also include the communication interface 26 that can be any means such as a device or circuitry embodied in either hardware or a combination of hardware and software that is configured to receive and/or transmit data from/to other electronic devices in communication with the apparatus, such as a database that stores data generated and/or employed by the processing circuitry 22. Additionally or alternatively, the communication interface can be configured to communicate in accordance with various wireless protocols including Global System for Mobile Communications (GSM), such as but not limited to Long Term Evolution (LTE). In this regard, the communication interface can include, for example, an antenna (or multiple antennas) and supporting hardware and/or software for enabling communications with a wireless communication network. In this regard, the communication interface can include, for example, an antenna (or multiple antennas) and supporting hardware and/or software for enabling communications with a wireless communication network. Additionally or alternatively, the communication interface can include the circuitry for interacting with the antenna(s) to cause transmission of signals via the antenna(s) or to handle receipt of signals received via the antenna(s). In some environments, the communication interface can alternatively or also support wired communication.

The apparatus 10 may also optionally include a user interface 28 that may, in turn, be in communication with the processing circuitry 22 to provide output to a user and, in some embodiments, to receive an indication of a user input. As such, the user interface may include a display and, in some embodiments, may also include a keyboard, a mouse, a joystick, a touch screen, touch areas, soft keys, one or more microphones, a plurality of speakers, or other input/output mechanisms. In one embodiment, the processing circuitry may comprise user interface circuitry configured to control at least some functions of one or more user interface elements such as a display and, in some embodiments, a plurality of speakers, a ringer, one or more microphones and/or the like. The processing circuitry and/or user interface circuitry embodied by the processing circuitry may be configured to control one or more functions of one or more user interface elements through computer program instructions (for example, software and/or firmware) stored on a memory accessible to the processing circuitry (for example, memory 24, and/or the like).

Referring now to FIG. 3, the operations performed, such as by the apparatus 20 of FIG. 2, in accordance with an example embodiment are depicted. As shown in block 30, the apparatus includes means, such as the processing circuitry 22, the communication interface 26 or the like, for causing first information provided by a request processor 14 in response to an inquiry to be provided to a source 16. The first information that is provided to the source may be provided in response to a variety of different conditions or requests. In an example embodiment, the source is configured to transmit an inquiry, such as via the apparatus, to the request processor and the request processor, in turn, causes the first information to be provided in response to the inquiry. Although the system of FIG. 1 is depicted to include one request processor, one source and one supplier 18 (which will be discussed below), the system may include any number of request processors, sources and suppliers in other embodiments. In an instance in which the system does include a plurality of request processors, the inquiry provided by a source may identify or include information from which the identity of the respective request processor to which the inquiry is directed may be identified such that the inquiry may be appropriately directed.

The apparatus 20 of an example embodiment is configured to form an updated order for at least a certain combination of the request processor 14 and the supplier 18, such as combinations of the request processor and the supplier in which both the request processor and the supplier are authorized to communicate via an updated order. In an instance in which the system 10 includes a plurality of suppliers, the inquiry provided by the source 16 may identify a respective supplier or may include information from which the identity of a respective supplier may be identified. Thus, the apparatus 20, such as the processing circuitry 22, of an example embodiment is configured to determine whether the combination of the request processor that provided the original inquiry and the supplier that is identified by the inquiry are both authorized to communicate via an updated order. In an instance in which the combination of request processor and the supplier associated with the original inquiry are authorized to communicate in accordance with an updated order and, in some embodiments, the item(s) that are to be subject of the updated order are also qualified for the updated order, the apparatus, such as the processing circuitry, the communication interface 26 or the like, is configured to include an indication, such as a flag, in combination with the first information provided by the request processor to the source. The indication, such as the flag, is indicative of the authorization of the request processor and the supplier identified by the original inquiry to subsequently communicate in accordance with an updated order that will be formed by the apparatus. If both the request processor and the supplier associated with the original inquiry are not authorized to communicate in accordance with an updated order or, in some embodiments, if the item(s) that are to be subject of the updated order are not qualified for the updated order, the indication, such as the flag, is not provided in combination with the first information and any subsequent order from the request processor that is directed to the supplier may be processed in accordance with a conventional technique, as opposed to the process depicted by FIG. 3.

As shown in block 32, the apparatus 20 also includes means, such as the processing circuitry 22, the memory 24 or the like, for storing the first information as provided by the request processor 14 in response to the inquiry from the source 14. The apparatus of an example embodiment also includes means, such as the processing circuitry, the communication interface 26 or the like, for receiving an order including second information, different then the first information, from the source. See block 34. In at least some embodiments, the order that is provided by the source is based at least in part upon the first information that is provided to the source by the request processor in response to the initial inquiry. In at least some embodiments, the order may be a request for one or more items to be provided by a supplier 16 with payment for the one or more items being at least partially provided in at least some instances by the source. The order may be provided by the source in a first format via which the source is configured to communicate.

As shown in block 36 of FIG. 3, the apparatus 20 of an example embodiment includes means, such as the processing circuitry 22 or like, for pre-processing the order and determining whether the order includes all of the data elements that are required for the order to be properly processed. In this regard, the apparatus, such as the processing circuitry, is configured to have access to information, such as stored by the memory 24 or by a database with which the apparatus is in communication, such as via the communication interface 26, that defines the data elements that are required for an order or at least certain types of orders. In an instance in which the order does not include all necessary data elements, the apparatus, such as the processing circuitry, is configured to further process the order in an effort to supplement the order with one or more additional data elements that are required, but that are not currently included in the order. The one or more additional data elements may be obtained in various manners.

For example, the apparatus 20 may include means, such as the processing circuitry 22, the communication interface 26 or the like, for communicating with the source 16 as shown in block 38 to obtain the one or more additional data elements with which to supplement the order. In this regard, the apparatus, such as the processing circuitry, the communication interface or the like, is configured to transmit a message to the source identifying the one or more data elements that should be provided, but that were not included in the order and to request that the source provide the one or more additional elements.

In an instance in which the one or more additional data elements that are not included in the order cannot be obtained, such as from the source 16, the order cannot be properly processed and the apparatus 20, such as the processing circuitry 22, the communication interface 26 or the like, is configured to notify the source of the failure to process the order and may request that the source subsequently submit an order including all required data fields if the source desires for the order to be properly processed.

However, in an instance in which the order submitted by the source 16 is complete and includes all required data elements or in an instance in which one or more necessary data elements are missing from the order, but are subsequently provided, such as by the additional information provided by the source in order to complete the order, the apparatus 20 of an example embodiment includes means, such as the processing circuitry 22 or the like, for converting the order to a second format, different then the first format in which the source submitted the order. See block 40 of FIG. 3. In this regard, the source may be configured to communicate in accordance with a first format while the supplier 18 that will subsequently process and respond to the order, such as by filling the order, may be configured to communicate in accordance with the second format, different than the first format. Thus, the apparatus, such as the processing circuitry, of this example embodiment is configured to provide for the conversion between the different formats in order to permit the request processor and the supplier to communicate seamlessly without requiring either the request processor or the supplier to format the order in a different manner then that in which they are currently configured.

As shown in block 42 of FIG. 3, the apparatus 20 also includes means, such as processing circuitry 22 or the like, for combining at least some of the second information provided with the order with at least some of the first information provided by the request processor 14 in response to the initial inquiry from the source 16. In this regard, the apparatus, such as the processing circuitry, of an example embodiment may be configured to access the first information that has been stored, such as the by the memory 24 or a database with which the apparatus is in communication, and to then combine the first information, or at least a portion of the first information, with at least some of the second information that is included within the order so as to form an updated order.

The apparatus 20, such as the processing circuitry 22, the communication interface 26 or the like, may then be configured to determine the supplier 18 to which the updated order should transmitted. In an example embodiment, the apparatus includes means, such as the processing circuitry, the communication interface or the like, for identifying the supplier that is the intended recipient of the order based upon the second information provided by the order. See block 44.

In this regard, the order may include an identifier or other information from which the identity of the supplier may be determined. In this example embodiment, the apparatus also includes means, such as the processing circuitry, the memory 24, the communication interface or the like, for accessing routing information for the supplier that has been identified to be the intended recipient of the order. See block 46 of FIG. 3. In this regard, a routing table or other address information may be stored, such as by the memory or by a database with which the apparatus is in communication, such that the apparatus, such as the processing circuitry, is configured to identify the address, such as the uniform resource location (URL) or other address, of the supplier that is the intended recipient of the updated order based upon the stored routing or other address information.

By processing the order provided by the source 16 and forming an updated order that satisfies the requirements of a supplier 18, the service provider 12 and, more particularly, the apparatus 20, such as the processing circuitry 22, of an example embodiment provides for seamless communication between the various parties without requiring the parties to be configured to communicate directly with one another and without requiring the parties to be configured to communicate in accordance with the same standard including in accordance with the same format. Thus, the apparatus, such as the processing circuitry, of this example embodiment facilitates communication between the parties and provides technical advantages by eliminating or reducing requirements for concurrent and identical configuration of the various parties in relation to the standards and other rules that govern communication therebetween. As shown in block 48 of FIG. 3, the apparatus 20 also includes means, such as the processing circuitry 22, the communication interface 26 or the like, for transmitting the updated order to the supplier 18, such as by directing the updated order to the address that has been identified for the supplier that is the intended recipient or the order.

In accordance with an example embodiment in which the supplier 18 that receives the order looks to a different party, such as the request processor 14 that responded to the initial inquiry from the source 16, for at least a portion of the payment for the one or more items that are the subject of the order, the apparatus 20 includes means, such as the processing circuitry 22 or the like, for monitoring an adjudication network established by or with the request processor in order to monitor the status of the order. See block 50 FIG. 3. In this regard, after receipt of the order, the supplier may not fill the order for some time, if at all, such as by not filling the order until another condition is satisfied that triggers filling of the order. In this situation, the supplier may also not submit the order, or information regarding the order, to the request processor in order to seek the at least partial payment by the request processor until such time that the other condition has been satisfied.

By monitoring the adjudication network and identifying the instance in which the supplier 18 has submitted the order, or information regarding the order, to the request processor 14 in order to seek at least partial payment, the apparatus 20, such as the processing circuitry 22 or the like, is configured to identify the change in status of the order, such as to a paid status, and to correlate the change in status to the fulfillment by the order by the supplier. Thus, the apparatus of this example embodiment may include means, such as the processing circuitry, the communication interface 26 or the like, for providing a notification to the source 16 that submitted the order in response to the order having a predetermined status, such as a paid status, that is indicative of the order having been filled. See block 52.

As a result of monitoring the adjudication network and providing a notification in an instance in which the order has a predetermined status, the source 16 that submitted order is assured of receiving feedback in an instance in which the order is processed. In this regard, the apparatus 20, such as the processing circuitry 22, the communication interface 26 or the like, may be configured to monitor the adjudication network for a predefined period of time. Thus, the source is assured of receiving a response regarding the status of the order within the predefined period of time, such as an indication that the order has been filled or that the order has not been filled (in an instance in which the predefined period of time expires without a change in the order status). Consequently, the source has less incentive to resubmit the order out of concern that the initial order was misdirected or otherwise not successfully received and processed and correspondingly reduces the burden upon the communication network and/or the computing devices of the various parties relative to instances in which the source resubmits the order.

As noted above, the method, apparatus 20 and computer program product of an example embodiment may be utilized in a wide variety of different applications. By way of example, but not of limitation, the method, apparatus and computer program product of an example embodiment are described hereinafter in relation to FIGS. 4-6 in which the initial inquiry is a prescription benefit coverage inquiry that determines the financial responsibility of a request processor 14 for a particular prescription and the subsequent order is a prescription order that triggers a prescription benefit coverage request to be directed to the request processor for the prescription order. In this example embodiment, the data and other information discussed below may therefore be stored and/or shared or otherwise transmitted pursuant to the Health Insurance Portability and Accountability Act (HIPAA) of 1996.

As shown in FIG. 4, a system 60 includes a service provider 12 which, in turn, includes an apparatus 20 as shown in FIG. 2 and described above. The system of FIG. 4 also includes one or more sources in the form of one or more prescribers 62 designated as Prescriber 1, Prescriber 2, . . . . Prescriber n in FIG. 4. A prescriber is a healthcare professional, such as a physician or other healthcare practitioner or practice or a healthcare system, such as an electronic healthcare record system operated or otherwise utilized by a physician or other healthcare practitioner to write and submit prescriptions for patients. Further, the system of this example embodiment includes one or more suppliers in the form of one or more pharmacies 64 designated as Pharmacy 1, Pharmacy 2, . . . Pharmacy n in the example embodiment of FIG. 4. These pharmacies may be brick and mortar pharmacies or may be online or other types of pharmacies that fill prescription orders. The system of this example embodiment also includes one or more request processors in the form of a pharmacy benefit management (PBM) entity or other payer, such as an insurance company or the like. Although FIG. 4 depicts a single request processor in the form of a PBM/Payer 66, the system of this example embodiment may, instead, include a plurality of PBMs/payers. As described below, the pharmacies are configured to communicate with the PBMs or other payers to provide at least partial payment for the prescription orders As shown in block 70 of FIG. 5A, the apparatus 20 embodied by the service processor 12 in accordance with an example embodiment includes means, such as the processing circuitry 22, the communication interface 26 or the like, for receiving the prescription benefit coverage inquiry from a prescriber 62. The prescription benefit coverage inquiry is submitted by the prescriber as shown in block 110 of FIG. 6 and identifies a particular medication or other item that may subsequently be the subject of a prescription order and may solicit information regarding the amount that a PBM or other payer 66 would pay on behalf of the patient in an instance in which the patient were to fill a prescription for the medication or other item.

Thus, the apparatus 20 is configured to determine the amount that the PBM or other payer 66 would pay on behalf of the patient once a prescription for the medication or other item identified by the prescription benefit coverage inquiry has been filled. This determination of the coverage amount may be performed in various manners. In one embodiment, the apparatus determines the coverage amount based on information provided by the PBM or other payer. As such, the apparatus, such as the processing circuitry 22, the communication interface 26 or the like, may be configured to process the prescription benefit coverage inquiry and to transmit the prescription benefit coverage inquiry or at least information provided by the prescription benefit coverage inquiry, to the PBM or other payer. See blocks 112 and 114 of FIG. 6. In this regard, the prescription benefit coverage inquiry may identify the respective PBM or other payer to which the prescription benefit coverage inquiry is directed such that the apparatus and, more particularly, the processing circuitry or the communication interface may be configured to identify the respective PBM or other payer to which the prescription benefit coverage inquiry is to be directed and then correspondingly provide the prescription benefit coverage inquiry or at least information provided by and related to the prescription benefit coverage inquiry to the respective PBM or other payer.

As shown in block 72, the apparatus 20 of this example embodiment also includes means, such as the processing circuitry 22, the communication interface 26 or the like, for obtaining a response to the prescription benefit coverage inquiry from the respective PBM or other payer 66. As shown in blocks 116 and 118 of FIG. 6, the PBM/payer processes the prescription benefit coverage inquiry and then returns the response. The response identifies the amount that the PBM or other payer would pay on behalf of the patient once a prescription for the medication or other item identified by the prescription benefit coverage inquiry has been filled.

In other embodiments, the apparatus 20 does not determine the coverage amount based on information provided by the PBM or other payer 66, but, instead, estimates the coverage amount, such as based on historical information. In this example embodiment, the apparatus includes means, such as the processing circuitry 22, the memory 24 or the like, for determining an estimate of the amount that a PBM or other payer would pay on behalf of the patient for a particular medication or other item. For example, the apparatus, such as the memory or another database with which the apparatus is in communication, may store historical information regarding the amount that a respective PBM or other payer has paid in the past for the same or similar quantity of the same medication having the same National Drug Code (NDC). In some embodiments, the historical information that is considered is also limited to historical information for the same pharmacy or chain of pharmacies in the same state. Further, the historical information that is considered may be limited to a most recent time period, such as an immediately preceding 60 day period. Based upon the historical information, the apparatus, such as the processing circuitry, is configured to determine the estimated amount that will be paid by the PBM or other payer.

In order to increase the confidence in the estimated amount, the apparatus 20, such as the processing circuitry 22, may be configured to require the historical amounts that the respective PBM or other payer has paid in the past to be within a predefined range, such as $10. In an instance in which the historical amounts that the respective PBM or other payer has paid in the past are not within the predefined range, the apparatus, such as the processing circuitry, may be configured to indicate that an estimated amount cannot be determined. However, in an instance in which the historical amounts that the respective PBM or other payer has paid in the past are within the predefined range, the apparatus, such as the processing circuitry, may be configured to determine an estimated amount in the form of a range of historical amounts paid by the PBM or other payer for the same or a similar quantity of the same medication having the same NDC. In some embodiments, any outlying historical amounts may be removed from consideration prior to determining the range of historical amounts. For example, the apparatus, such as the processing circuitry, may be configured to construct a distribution of the historical amounts and to then define the range of the historical amounts that will form the estimated amount to be within a predefined range of the mean of the distribution, such as within one or a predefined number, e.g., 2, of standard deviations of the mean.

The apparatus 20, such as the processing circuitry 22, may be configured to determine whether to provide the response to the prescription benefit coverage inquiry based upon the information provided by a PBM or other respective payer 66 or based upon an estimate that relies upon historical information in various manners. For example, the apparatus, such as the processing circuitry, may be configured to initially attempt to obtain the coverage amount from the respective PBM or other payer and to only determine a estimate of the coverage amount based upon historical information in an instance in which the coverage amount cannot be obtained from the respective PBM or other payer, such as an instance in which the respective PBM or other payer does not respond or in an instance in which the prescription benefit coverage inquiry does not identify a respective PBM or other payer and/or does not provide the necessary eligibility data for the patient. Alternatively, the apparatus, such as the processing circuitry, may be configured to initially determine an estimate of the coverage amount based upon historical information in an instance in which both the prescription benefit coverage inquiry provided sufficient information to allow for such an estimate and in which sufficient historical information is accessible to allow the estimate to be performed. In this example embodiment in which there is an initial attempt to estimate the coverage amount, the apparatus, such as the processing circuitry, the communication interface 26 or the like, is configured to only solicit a response from the respective PBM or other payer in an instance in which an estimated amount cannot be determined. Thus, the apparatus of this example embodiment limits communication with the PBM or other payer, thereby conserving network resources that would otherwise be consumed for the communications with the respective PBM or other payer and also conserving computing resources of the respective PBM or other payer.

The apparatus 20 of an example embodiment also includes means, such as the processing circuitry 22, the memory 24 or the like, for determining whether both the prescriber 62 and the pharmacy 64 to which a subsequent prescription order for the patient will be directed are able to utilize an updated order. See block 74 of FIG. 5A as well as blocks 120 and 122 of FIG. 6. In this regard, the pharmacy to which a subsequent prescription order for the patient will be directed may be identified by the prescription benefit coverage inquiry or may be based upon information stored by the memory or by a database with which the apparatus has access which identifies the respective pharmacy associated with the patient that is the subject of the prescription benefit coverage inquiry. In addition, the apparatus, such as memory or a database with which the apparatus has access, is also configured to identify whether the prescriber and the pharmacy are authorized to utilize the updated order that is constructed in accordance with an example embodiment, such as based upon a listing of the prescribers and pharmacies authorized to utilize an updated order, such the prescribers and pharmacies that have subscribed to or have otherwise been configured to utilize an updated order.

In an instance in which the prescriber 62 and the pharmacy 64 are configured to utilize an updated order, the updated order may be utilized in conjunction with any type of medication, refill or other prescribed item. In other embodiments, however, not only must the prescriber 62 and the pharmacy 64 be authorized to utilize the updated order, but the updated order may only be utilized in conjunction with certain medications or other items. Thus, the apparatus 20, such as the processing circuitry 22, of this example embodiment is optionally configured to determine whether the medication or other item identified by the prescription benefit coverage inquiry is able to be the subject of an updated order, such as by comparing the medication or other item identified by the prescription benefit coverage inquiry to a list of medications or other items, such as may be stored by memory 24 or by a database with which the apparatus is in communication, that are authorized to be the subject of an updated order.

In an instance in which an updated order may not be utilized, such as based upon a failure of the prescriber 62 or the pharmacy 64 of the respective patient to be authorized to utilized the updated order or in an instance in which the medication or other item that is the subject of the prescription benefit coverage inquiry is not authorized to be the subject of an updated order, the apparatus 20 includes means, such as the processing circuitry 22, the communication interface 26 or the like, for causing information regarding the prescription benefit coverage as provided by the respective PBM or other payer 66 or as based upon an estimated amount may be provided to the prescriber as shown in block 76 and the process of FIGS. 5A and 5B may be terminated.

However, in an instance in which the updated order is able to be utilized as shown in block 126 of FIG. 6, the apparatus 20 of an example embodiment also includes means, such as a processing circuitry 22, the communication interface 26 or the like, for causing information regarding the prescription benefit coverage to be provided in combination with an indication, such as a flag, indicating that the updated order may be utilized. See block 78 of FIG. 5A. In this regard, the information regarding the prescription benefit coverage may be provided by the respective PBM or other payer 66 or may be an estimated amount provided based upon historical information as described above. As shown in blocks 128 and 130 of FIG. 6, for example, information regarding the prescription benefit coverage is sent by the apparatus, such as the communication interface, and received by the prescriber 62.

The apparatus 20 of this example embodiment also includes means, such the processing circuitry 22, the memory 24 or the like, for storing at least some of the information regarding the prescription benefit coverage as shown in block 80 including at least some of the information presented to the prescriber 62. The apparatus also includes means, such as the processing circuitry, the communication interface 26 or the like, for thereafter receiving a prescription order from the prescriber. See block 82 of FIG. 5A. In this regard, the prescription order that is created by the prescriber as shown in block 132 of FIG. 6 may be based at least in part upon the information that has been provided regarding the prescription benefit coverage. For example, the prescriber and/or the patient may determine that a prescription order is to be placed for the medication or other item in an instance in which the prescription benefit coverage will be sufficient to permit the patient to afford the medication or other item. The prescription order includes clinical information, such as the name, the quantity, the days supply and the strength of a drug to be dispensed and/or the name and strength of each ingredient to be compounded. In some embodiments, the clinical information included in the prescription order is defined by the standard, such as the National Council for Prescription Drug Programs (NCPDP) SCRIPT standard, that governs the information that must be included in the order that is submitted to the pharmacy. In addition, the prescription order is generally formatted in accordance with a first predefined format, such as a Health Level 7 (HL7) or another predefined format that is commonly utilized by prescribers and the electronic healthcare record systems employed by prescribers in conjunction with this submission of prescription order.

In order to avoid the consumption of network resources and the computing resources of the pharmacies 64 and PBMs or other payers 66 in relation to a prescription order that is incomplete, the apparatus 20 of an example embodiment includes means, such as the processing circuitry 22 or the like, for pre-processing the prescription order to determine whether all necessary data elements of the prescription order have been provided. See block 84 as well as block 134 of FIG. 6 in which the data elements are validated. In this regard, the apparatus, such as the memory 24 or a database with which the apparatus is in communication, may include information defining the necessary data elements for a prescription order or the necessary data elements for certain types of prescription orders, such as the data elements defined by the standard, e.g., the NCPDP SCRIPT standard, that governs the information that must be included in the order that is submitted to the pharmacy. In an instance in which the prescription order is determined not to include all necessary data elements, the apparatus, such as the processing circuitry, is configured to further process the prescription order in an effort to supplement the prescription order with one or more additional data elements that are required, but that are not currently included in the prescription order.

The one or more additional data elements may be obtained in various manners. For example, the apparatus 20 may include means, such as the processing circuitry 22, the communication interface 26 or the like, for communicating with the prescriber 62 as shown in block 86 to obtain the one or more additional data elements with which to supplement the prescription order. In this regard, the apparatus, such as the processing circuitry, the communication interface or the like, is configured to transmit a message to the prescriber identifying the one or more data elements that should be provided, but that were not included in the prescription order and to request that the prescriber provide the one or more additional elements.

In an instance in which the one or more additional data elements that are not included in the prescription order are not provided by the prescriber 62, the prescription order cannot be properly processed and the apparatus 20, such as the processing circuitry 22, the communication interface 26 or the like, is configured to notify the prescriber of the failure to process the prescription order and may request that the prescriber subsequently submit a prescription order including all required data fields if the prescriber desires for the prescription order to be properly processed.

However, in an instance in which the prescription order submitted by the prescriber 62 is complete and includes all required data elements or in an instance in which one or more necessary data elements are missing from the prescription order, but are subsequently provided by reference to historical information or to additional information provided by the prescriber in order to complete the prescription order, the apparatus 20 of an example embodiment includes means, such as the processing circuitry 22 or the like, for converting the prescription order to a different format. See block 88 of FIG. 5A and block 136 of FIG. 6. In this regard, the apparatus, such as the processing circuitry, is configured to convert the prescription order to a second format, different than the first format. The second format may be a format with which the pharmacy 64 to which the prescription order will be directed is configured to communicate, such as the NCPDP format. As such, the apparatus, such as the processing circuitry, of this example embodiment allow for prescribers and pharmacies to communicate seamlessly and efficiently even though the prescribers and pharmacies are configured to transmit and receive differently formatted messages.

By processing the prescription order provided by the prescriber 62 and converting the prescription order to a format that satisfies the requirements of a pharmacy 64, the service provider 12 and, more particularly, the apparatus 20, such as the processing circuitry 22, of an example embodiment provides for seamless communication between the prescriber and the pharmacy without requiring the prescriber and the pharmacy to be configured to communicate directly with one another and without requiring the prescriber and the pharmacy to be configured to communicate in accordance with the same standard including in accordance with the same format. Thus, the apparatus, such as the processing circuitry, of this example embodiment facilitates communication between the prescriber and the pharmacy and provides technical advantages by eliminating or reducing requirements for concurrent and identical configuration of the prescriber and the pharmacy in relation to the standards and other rules that govern communication therebetween.

As shown in block 90 of FIG. 5B and block 140 of FIG. 6, the apparatus 20 of an example embodiment also includes means, such as the processing circuitry 22 or the like, for combining at least some of the clinical information provided in conjunction with the prescription order with at least some of the information regarding the prescription benefit coverage so as to form an updated prescription order. In this regard, the information regarding the prescription benefit coverage that is provided to the prescriber 62 and that may be presented or displayed to the prescriber may also be provided with the updated prescription order to the pharmacy 64 such that the pharmacy has ready access to that same information and both the prescriber and the pharmacy are equally informed and the pharmacy will have an understanding of the patient's expectations.

Once the updated prescription order has been formed, the apparatus 20 of this example embodiment includes means, such as the processing circuitry 22, the communication interface 26 or the like, for determining the pharmacy 64 to which the updated prescription order should transmitted. In an example embodiment, the apparatus includes means, such as the processing circuitry, the communication interface 26 or the like, for identifying the pharmacy that is the intended recipient of the prescription order based upon information provided by the prescription order. See block 92. In this regard, the prescription order may include an identifier, such as a national provider identifier (NPI) or a NCPDP identifier (ID), or other information from which the identity of the pharmacy may be determined. In this example embodiment, the apparatus also includes means, such as the processing circuitry, the memory 24, the communication interface or the like, for accessing routing information for the pharmacy that has been identified to be the intended recipient of the prescription order. See block 94 of FIG. 5B. In this regard, a routing table or other address information may be stored, such as by the memory or by a database with which the apparatus is in communication, such that the apparatus, such as the processing circuitry, is configured to identify the address, such as the URL or other address, of the supplier that is the intended recipient of the updated order based upon the stored routing or other address information.

As shown in block 96 of FIG. 5B, the apparatus 20 also includes means, such as the processing circuitry 22, the communication interface 26 or the like, for transmitting the updated order to the pharmacy 64, such as by directing the updated prescription order to the address or via the connection that has been assigned for the pharmacy that is the intended recipient or the order. As shown in blocks 142 and 144 of FIG. 6, the pharmacy receives the updated prescription order and then returns a confirmation of receipt of the updated prescription order, which is then relayed by the service provider 12 for receipt by the prescriber as shown in blocks 146 and 148. In an instance in which the updated prescription order, such as the information regarding the prescription benefit coverage that is included with the updated prescription order, indicates that a PBM/payer 66 will pay for a least a portion of the cost associated with the prescription, the apparatus 20 includes means, such as the processing circuitry 22 or the like, for monitoring an adjudication network established by or with the PBM/payer in order to monitor the status of the order since the pharmacy will likely submit a prescription claim on behalf of the patient for the updated prescription order as shown in block 150 of FIG. 6. See block 98 FIG. 5B and block 152 of FIG. 6. In this regard, the adjudication network is a network established between and utilized by the pharmacy and the PBM/payer in order to process prescription claims. Thus, the adjudication network allows a pharmacy to send a prescription claim to the PBM/payer to obtain the patient's out of pocket expense or, alternatively, to receive a denial from the PBM/payer. If a denial is received, the denial will indicate to the pharmacy what has to be done in order for the PBM/payer to approve the claim, e.g. obtain prior authorization, prescription is for a medication that is not covered, etc. The claim being processed on the adjudication network informs the pharmacy as to the amount to charge the patient and how much of the prescription costs will be reimbursed by the PBM/payer.

After receipt of the updated prescription order, the pharmacy 64 may fill the prescription such that the prescription will be ready when a patient arrives at the pharmacy to pick up the filled prescription. In this situation, the pharmacy may also submit the prescription claim on behalf of the patient to the PBM/payer in order to obtain the information defining the patient out-of-pocket costs as well as the amount that will be paid by the PBM/payer for the prescription.

By monitoring the adjudication network and identifying the instance in which the pharmacy 64 has submitted the prescription claim to the PBM/payer 66 in order to determine the financial responsibility of the patient and the PBM/payer for the prescription, the apparatus 20, such as the processing circuitry 22 or the like, is configured to identify a change in status of the prescription order, such as to a paid status as shown in block 154 of FIG. 6, and to correlate the change in status to the processing of the prescription order via the adjudication network by the pharmacy. Thus, the apparatus of this example embodiment may include means, such as the processing circuitry, the communication interface 26 or the like, for providing a notification to the prescriber 62 that submitted the prescription order in response to the prescription claim associated with the prescription order having a predetermined status, such as a paid status, that is indicative of the prescription order having been filled. See block 100 of FIG. 5B and blocks 156 and 58 of FIG. 6.

As a result of monitoring the adjudication network and providing a notification in an instance in which the prescription order has a predetermined status, such as a paid status indicative of the prescription having been filled, the prescriber 62 that submitted the prescription order is assured of receiving feedback in an instance in which the prescription order is processed. In this regard, the apparatus 20, such as the processing circuitry 22, the communication interface 26 or the like, may be configured to monitor the adjudication network for a predefined period of time once the prescription order is assigned the predetermined status, such as the paid status, indicating that the prescription order has been filled. In this regard, the pharmacy 64 may operate in accordance with internal processes that dictate that a prescription order that has been filled, but that has not been picked up by the patient, is restocked following expiration of predetermined amount of time, such as five, seven, ten or any predefined number of days. Upon restocking, the pharmacy may update the status of the prescription order, such as from a status of paid to a status of reversed. By monitoring the adjudication network for a predefined period of time, such as 14, 21, 28 or any predefined number of days, that is longer than the predetermined amount of time in which restocking occurs, the apparatus, such as the processing circuitry, is configured to distinguish between a prescription order that is filled and then picked up by the patient (for which the status remains as paid throughout the predefined period of time) and a prescription order that is filled, but that is not picked up by the patient and is restocked (for which the status is updated from paid to reversed during the predefined period of time). In this example embodiment, the apparatus, such as the processing circuitry, the communication interface or the like, may be configured to inform the prescriber of the status of the prescription order following the predefined period of time, such as by informing the prescriber as to whether the prescription order is filled or reversed. Thus, the prescriber is assured of receiving a response regarding the status of the prescription order within the predefined period of time, such as an indication that the prescription has been filled and picked up by the patient or that the prescription has not been picked up by the patient. Consequently, the prescriber has less incentive to resubmit the prescription order out of concern that the initial prescription order was misdirected or otherwise not successfully received and processed and correspondingly reduces the burden upon the communication network and/or the computing devices of the prescriber and the pharmacy relative to instances in which the prescriber resubmits the prescription order. Moreover, the prescriber will be more informed during subsequent treatment of the patient by knowing whether or not the patient picked up the medication that was previously prescribed.

As noted above, FIGS. 3, 5A, 5B and 6 are flowcharts illustrating the operations performed by a method, apparatus and computer program product, such as apparatus 20 of FIG. 2, in accordance with one embodiment of the present invention. It will be understood that each block of the flowcharts, and combinations of blocks in the flowcharts, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory 24 of a computing device employing an embodiment of the present invention and executed by a processing circuitry 22 of the apparatus. As will be appreciated, any such computer program instructions may be loaded onto a computer or other programmable apparatus (e.g., hardware) to produce a machine, such that the resulting computer or other programmable apparatus provides for implementation of the functions specified in the flowchart blocks. These computer program instructions may also be stored in a non-transitory computer-readable storage memory that may direct a computer or other programmable apparatus to function in a particular manner, such that the instructions stored in the computer-readable storage memory produce an article of manufacture, the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks. As such, the operations of FIGS. 3, 5A, 5B and 6, when executed, convert a computer or processing circuitry into a particular machine configured to perform an example embodiment of the present invention. Accordingly, the operations of FIGS. 3-6 define an algorithm for configuring a computer or processing circuitry, e.g., processor, to perform an example embodiment. In some cases, a general purpose computer may be provided with an instance of the processor which performs the algorithm of FIGS. 3, 5A, 5B and 6 to transform the general purpose computer into a particular machine configured to perform an example embodiment.

Accordingly, blocks of the flowcharts support combinations of means for performing the specified functions and combinations of operations for performing the specified functions. It will also be understood that one or more blocks of the flowcharts, and combinations of blocks in the flowcharts, can be implemented by special purpose hardware-based computer systems which perform the specified functions, or combinations of special purpose hardware and computer instructions. In some embodiments, certain ones of the operations above may be modified or further amplified and additional optional operations may be included. It should be appreciated that each of the modifications, optional additions or amplifications below may be included with the operations above either alone or in combination with any others among the features described herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for monitoring an adjudication network, the method comprising:
    causing first information provided by a request processor in response to an inquiry to be provided to a source, wherein the request processor comprises a pharmacy benefit management (PBM) entity or other payer, the inquiry comprises a prescription benefit coverage inquiry that identifies a medication or other item and the first information relates to an amount that the PBM entity or other payer would pay on behalf of a patient if the patient were to file a prescription for the medication or other item;
    storing the first information provided by the request processor in response to the inquiry;
    receiving an order including second information, different than the first information, from the source, wherein the order and the inquiry are different types of messages, wherein the order comprises a prescription order for the medication or other item that includes clinical information and is received in accordance with a first format with which the source is configured to communicate, and wherein the source comprises a prescriber and the first format comprises a Health Level 7 (HL7) format utilized by a system of the prescriber;
    converting the order to a second format with which a supplier is configured to communicate, wherein the second format is different than the first format, and wherein the supplier comprises a pharmacy and the second format comprises a National Council for Prescription Drug Programs (NCPDP) format via which the pharmacy is to communicate;
    accessing the first information that has been stored;
    combining at least one aspect of the second information following conversion to the second format, with at least one aspect of the first information that has been stored and subsequently accessed to form an updated order;
    transmitting the updated order to the supplier;
    monitoring the adjudication network to determine a status of the updated order; and
    providing a notification to the source in response to the updated order having a predefined status indicative of the updated order having been filled.

2. A method according to claim 1 wherein monitoring the adjudication network comprises monitoring the adjudication network for a predefined period of time.

3. A method according to claim 1 further comprising:
    processing the order to identify whether all required data elements have been provided; and
    in an instance in which one or more of the required data elements have not been provided, communicating with the source to obtain the one or more required data elements prior to combining the at least one aspect of the second information with at least one aspect of the first information.

4. A method according to claim 1 further comprising:
determining whether the source and the supplier are able to utilize the updated order; and
in an instance in which the source and the supplier are able to utilize the updated order, providing an indication to the source in association with the first information.

5. A method according to claim 1 further comprising:
identifying the supplier based upon the second information of the order; and
accessing predetermined routing information to identify address information associated with the supplier.

6. A method according to claim 1 further comprising accessing historical information in an attempt to obtain the first information to respond to the inquiry and soliciting the first information from the request processor in an instance in which the first information cannot be determined from the historical information.

7. An apparatus configured to monitor an adjudication network, the apparatus comprising:
a communication interface configured to cause first information provided by a request processor in response to an inquiry to be provided to a source and to receive an order including second information, different than the first information, from the source, wherein the order and the inquiry are different types of messages, wherein the order comprises a prescription order for a medication or other item that includes clinical information and is received in accordance with a first format with which the source is configured to communicate, wherein the source comprises a prescriber and the first format comprises a Health Level 7 (HL7) format utilized by a system of the prescriber, wherein the request processor comprises a pharmacy benefit management (PBM) entity or other payer, the inquiry comprises a prescription benefit coverage inquiry that identifies the medication or other item and the first information relates to an amount that the PBM entity or other payer would pay on behalf of a patient if the patient were to file a prescription for the medication or other item;
a memory device configured to store the first information provided by the request processor in response to the inquiry; and
processing circuitry configured to convert the order to a second format with which a supplier is configured to communicate, wherein the second format is different than the first format, and wherein the supplier comprises a pharmacy and the second format comprises a National Council for Prescription Drug Programs (NCPDP) format via which the pharmacy is to communicate,
wherein the processing circuitry is also configured to access the first information stored by memory device and to combine at least one aspect of the second information, following conversion to the second format, with at least one aspect of the first information that has been stored by the memory device and subsequently accessed to form an updated order for transmission by the communication interface to the supplier, wherein the processing circuitry is also configured to monitor the adjudication network to determine a status of the updated order,
wherein the communication interface is also configured to provide a notification to the source in response to the updated order being determined by the processing circuitry to have a predefined status indicative of the updated order having been filled.

8. An apparatus according to claim 7 wherein the processing circuitry is configured to monitor the adjudication network by monitoring the adjudication network for a predefined period of time.

9. An apparatus according to claim 7 wherein the processing circuitry is further configured to process the order to identify whether all required data elements have been provided, and wherein, in an instance in which one or more of the required data elements have not been provided, the communication interface is further configured to communicate with the source to obtain the one or more required data elements prior to combining the at least one aspect of the second information with at least one aspect of the first information.

10. An apparatus according to claim 7 wherein the processing circuitry is further configured to determine whether the source and the supplier are able to utilize the updated order, and wherein the communication interface is further configured, in an instance in which the source and the supplier are able to utilize the updated order, to provide an indication to the source in association with the first information.

11. An apparatus according to claim 7 wherein the processing circuitry is further configured to identify the supplier based upon the second information of the order and to access predetermined routing information to identify address information associated with the supplier.

12. An apparatus according to claim 7 wherein the processing circuitry is further configured to access historical information in an attempt to obtain the first information to respond to the inquiry, and wherein the communication interface is further configured to solicit the first information from the request processor in an instance in which the first information cannot be determined from the historical information.

13. A computer program product configured to monitor an adjudication network, the computer program product comprising at least one non-transitory computer-readable storage medium having computer-executable program code instructions stored therein, the computer-executable program code instructions comprising program code instructions configured to:
cause first information provided by a request processor in response to an inquiry to be provided to a source, wherein the request processor comprises a pharmacy benefit management (PBM) entity or other payer, the inquiry comprises a prescription benefit coverage inquiry that identifies a medication or other item and the first information relates to an amount that the PBM entity or other payer would pay on behalf of a patient if the patient were to file a prescription for the medication or other item;
store the first information provided by the request processor in response to the inquiry;
receive an order including second information, different than the first information, from the source, wherein the order and the inquiry are different types of messages, wherein the order comprises a prescription order for the medication or other item that includes clinical information and is received in accordance with a first format with which the source is configured to communicate, and wherein the source comprises a prescriber and the first format comprises a Health Level 7 (HL7) format utilized by a system of the prescriber;
convert the order to a second format with which a supplier is configured to communicate, wherein the second format is different than the first format, and wherein the supplier comprises a pharmacy and the second format comprises a National Council for Prescription Drug Programs (NCPDP) format via which the pharmacy is to communicate;

access the first information that has been stored;

combine at least one aspect of the second information, following conversion to the second format, with at least one aspect of the first information to form an updated order;

cause the updated order to be transmitted the supplier;

monitor the adjudication network to determine a status of the updated order; and cause a notification to be provided to the source in response to the updated order having a predefined status indicative of the updated order having been filled.

14. A computer program product according to claim 13 wherein the program code instructions configured to monitor the adjudication network comprise program code instructions configured to monitor the adjudication network for a predefined period of time.

15. A computer program product according to claim 13 wherein the program code instructions are further configured to:

process the order to identify whether all required data elements have been provided; and in an instance in which one or more of the required data elements have not been provided, cause the source to be alerted to solicit the one or more required data elements prior to combining the at least one aspect of the second information with at least one aspect of the first information.

16. A computer program product according to claim 13 wherein the program code portions are further configured to:

determine whether the source and the supplier are able to utilize the updated order; and in an instance in which the source and the supplier are able to utilize the updated order, cause an indication to be provided to the source in association with the first information.

17. A computer program product according to claim 13 wherein the program code instructions are further configured to access historical information in an attempt to obtain the first information to respond to the inquiry and soliciting the first information from the request processor in an instance in which the first information cannot be determined from the historical information.

* * * * *